United States Patent
Kitching (10) Patent No.: US 10,383,704 B2
(45) Date of Patent: Aug. 20, 2019

(54) DIRECT MANUFACTURE OF ORTHODONTIC ALIGNER APPLIANCE

(71) Applicant: Ormco Corporation, Orange, CA (US)

(72) Inventor: Ian Kitching, San Dimas, CA (US)

(73) Assignee: Ormco Corporation, Orange, CA (US)

( * ) Notice: Subject to any disclaimer, the term of this patent is extended or adjusted under 35 U.S.C. 154(b) by 1285 days.

(21) Appl. No.: 13/738,513

(22) Filed: Jan. 10, 2013

(65) Prior Publication Data

US 2013/0122448 A1    May 16, 2013

Related U.S. Application Data

(63) Continuation-in-part of application No. 13/650,886, filed on Oct. 12, 2012, now abandoned.

(Continued)

(51) Int. Cl.
*A61C 7/00*      (2006.01)
*A61C 7/08*      (2006.01)

(Continued)

(52) U.S. Cl.
CPC ............. *A61C 7/002* (2013.01); *A61C 7/08* (2013.01); *A61C 7/36* (2013.01); *B33Y 80/00* (2014.12)

(58) Field of Classification Search
CPC ............. A61C 7/002; A61C 7/08; A61C 7/00; A61C 13/0004

(Continued)

(56) References Cited

U.S. PATENT DOCUMENTS 3,502,466 A    3/1970   Vickery
4,844,144 A    7/1989   Murphy et al.

(Continued)

FOREIGN PATENT DOCUMENTS

DE    10 2008 061325 A1    4/2010
EP    2581062 A2    4/2013

(Continued)

OTHER PUBLICATIONS

Yamamoto, K. et al., Optical measurement of Dental Case Profile and Appliation to Analysis of Three-Dimensional Tooth Movement in Orthodontics, Frontiers of Medical and Biological Engineering, vol. 1, No. 2, pp. 119-130 (1988).

(Continued)

*Primary Examiner* — Wade Miles
*Assistant Examiner* — Matthew P Saunders
(74) *Attorney, Agent, or Firm* — Wood Herron & Evans LLP (57) ABSTRACT

A method for fabrication of an orthodontic device having tooth-fitting cavities, such as an aligner, using layer-by-layer printing of a single or multiple polymeric materials. The cavities of the appliance or an appliance mold are defined by the boundaries of the multiple layers, encapsulating up to fourteen teeth of a patient, and shaped to apply a load to at least one tooth that is sufficient to cause movement of the tooth, and remodeling of the adjacent bone. In the case where the cavities form an appliance mold, the mold is used to form a positive model and an appliance is formed thereon. A series of such appliances may be used to treat malocclusion of teeth, each appliance used in series to incrementally move one or more teeth from initial positions toward a desired final position. The appliance may be fabricated with a variety of disclosed materials, and may include auxiliary features for interaction with other orthodontic elements.

13 Claims, 9 Drawing Sheets

Related U.S. Application Data (60) Provisional application No. 61/546,554, filed on Oct. 12, 2011.

(51) Int. Cl.
*A61C 7/36* (2006.01)
*B33Y 80/00* (2015.01)

(58) Field of Classification Search
USPC .................................................. 433/2–24
See application file for complete search history.

(56) References Cited

U.S. PATENT DOCUMENTS

| | | |
|---|---|---|
| 5,131,844 A | 7/1992 | Marinaccio et al. |
| 5,136,515 A | 8/1992 | Helinski |
| 5,139,419 A | 8/1992 | Andreiko et al. |
| 5,368,478 A | 11/1994 | Andreiko et al. |
| 5,395,238 A | 3/1995 | Andreiko et al. |
| 5,431,562 A | 7/1995 | Andreiko et al. |
| 5,447,432 A | 9/1995 | Andreiko et al. |
| 5,454,717 A | 10/1995 | Andreiko et al. |
| RE35,169 E | 3/1996 | Lemchen et al. |
| 5,510,066 A | 4/1996 | Fink et al. |
| 5,512,162 A | 4/1996 | Sachs et al. |
| 5,518,397 A | 5/1996 | Andreiko et al. |
| 5,542,842 A | 8/1996 | Andreiko et al. |
| 5,683,243 A | 11/1997 | Andreiko et al. |
| 5,823,778 A | 10/1998 | Schmitt et al. |
| 5,879,158 A | 3/1999 | Doyle et al. |
| 5,975,893 A * | 11/1999 | Chishti et al. .................. 433/6 |
| 6,015,289 A | 1/2000 | Andreiko et al. |
| 6,200,135 B1 | 3/2001 | Hultgren |
| 6,205,716 B1 | 3/2001 | Peltz |
| 6,210,162 B1 | 4/2001 | Chishti et al. |
| 6,217,334 B1 | 4/2001 | Hultgren |
| 6,227,850 B1 | 5/2001 | Chishti et al. |
| 6,244,861 B1 | 6/2001 | Andreiko et al. |
| 6,322,728 B1 | 11/2001 | Brodkin et al. |
| 6,471,512 B1 | 10/2002 | Sachdeva et al. |
| 6,532,394 B1 | 3/2003 | Earl et al. |
| 6,575,751 B1 | 6/2003 | Lehmann et al. |
| 6,616,444 B2 * | 9/2003 | Andreiko et al. ................. 433/3 |
| 6,846,179 B2 | 1/2005 | Chapouland et al. |
| 7,641,828 B2 * | 1/2010 | DeSimone et al. ........... 264/129 |
| 7,802,987 B1 | 9/2010 | Phan |
| 2001/0002310 A1 | 5/2001 | Chishti et al. |
| 2002/0006597 A1 | 1/2002 | Andreiko et al. |
| 2003/0003416 A1 | 1/2003 | Chishti et al. |
| 2006/0093982 A1 | 5/2006 | Wen |
| 2006/0177789 A1 * | 8/2006 | O'Bryan ........................... 433/6 |
| 2007/0065768 A1 | 3/2007 | Nadav |
| 2008/0138767 A1 * | 6/2008 | Kuo et al. ..................... 433/167 |
| 2008/0254402 A1 * | 10/2008 | Hilliard ........................... 433/24 |
| 2008/0268400 A1 | 10/2008 | Moss et al. |
| 2009/0029310 A1 | 1/2009 | Pumphrey et al. |
| 2009/0118601 A1 | 5/2009 | Rabolt et al. |
| 2010/0219546 A1 * | 9/2010 | Puttler et al. ................... 264/16 |
| 2011/0039223 A1 | 2/2011 | Li et al. |
| 2011/0165533 A1 * | 7/2011 | Li et al. ......................... 433/24 |

FOREIGN PATENT DOCUMENTS

| | | |
|---|---|---|
| JP | 5168654 A | 7/1993 |
| JP | 3380553 A | 9/1996 |
| JP | 2008-531234 A | 8/2008 |
| JP | 2009 202033 A | 9/2009 |
| JP | 2010-501258 A | 1/2010 |
| JP | 2010-540087 A | 12/2010 |
| JP | 5253248 B2 | 7/2013 |
| WO | 9410935 A1 | 5/1994 |
| WO | 98/58596 A1 | 12/1998 |
| WO | 99/23973 A1 | 5/1999 |
| WO | 2006/096558 A2 | 9/2006 |
| WO | 2008/024450 A1 | 2/2008 |
| WO | 2008047090 A1 | 4/2008 |
| WO | 2009/042378 A1 | 4/2009 |
| WO | 2009/118601 A2 | 10/2009 |
| WO | 01/47405 A2 | 7/2011 |

OTHER PUBLICATIONS

Crawford, P.R., CAD/CAM in the Dental Office: Does it Work?, Journal, vol. 57, No. 2, pp. 121-123, Feb. 1991.

Biggerstaff, R.N., Computerized Diagnostic Setups and Simulations, The Angle Orthodontist, vol. 40, No. 1, pp. 28-36, Jan. 1978.

European Search Report, related corresponding application No. EP 14 15 0499, dated Apr. 15, 2014.

European Search Report dated Jun. 10, 2015, related to corresponding application No. EP 12188405.0 filed Oct. 12, 2012.

* cited by examiner

DIRECT MANUFACTURE OF ORTHODONTIC ALIGNER APPLIANCE

RELATED APPLICATION

The Present application is a continuation-in-part of U.S. patent application Ser. No. 13/650,886 filed Oct. 12, 2012, and claims priority to U.S. Patent Application Ser. No. 61/546,554 filed Oct. 12, 2011, the disclosure of each of which is hereby incorporated herein by reference in its entirety.

FIELD OF THE INVENTION

The present invention is directed to an orthodontic appliance and particularly to orthodontic aligners.

BACKGROUND OF THE INVENTION

In conventional orthodontic treatment, an orthodontist or an assistant affixes an orthodontic appliance, such as orthodontic brackets, to the patient's teeth and engages an archwire into a slot of each bracket. The archwire applies corrective forces that coerce the teeth to move into orthodontically correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable latch or slide for captivating the archwire within the bracket slot.

Conventional orthodontic brackets are ordinarily formed from stainless steel, which is strong, nonabsorbent, weldable, and relatively easy to form and machine. Patients undergoing orthodontic treatment using metal orthodontic brackets, however, may be embarrassed by the visibility of metal, which is not cosmetically pleasing. To address the unsightliness of metal brackets, certain conventional orthodontic brackets incorporate a bracket body of a transparent or translucent non-metallic material, such as a clear or translucent polymer or a clear or translucent ceramic that assumes the color or shade of the underlying tooth.

Alternatives to orthodontic brackets include other clear or less visible appliances. The most common of these are the so-called "aligners" that are interchangeable by the patient during treatment. The clinician may prescribe a series of aligners, which are generally placed over but are not themselves adhesively secured or otherwise attached to the patient's teeth, to move one or more teeth from their original position to their aesthetically pleasing position. Typically, a series of aligners is required to fully treat the patient because the degree of movement produced by an aligner is limited. As such, when used in a series, each aligner in the series may be designed to fulfill a portion of the treatment process or move one or more teeth over a portion of the entire distance toward the desired position.

One such aligner is the Invisalign® system available from Align Technology, Inc. The Invisalign® system includes removable aligners that are to be worn by the patient. Generally, these aligners are clear or transparent polymer orthodontic devices that are removably positioned over the teeth of the maxilla and/or the teeth of the mandible. By this system, as treatment progresses, the patient removes one aligner having a specific prescription and replaces it with another aligner having a second, different prescription. Each aligner is responsible for moving the teeth toward their final predetermined or aesthetically correct position.

The Invisalign® aligners are fabricated by way of a physical and computer aided molding process. The method begins by forming an impression of the patent's dentition using a suitable impression material, such as polyvinylsiloxane (PVS). The impression is scanned by CT from which a computer creates a three-dimensional digital positive model of the patient's teeth and gingival. To create an appliance to reflect the next desired tooth configuration in the series of treatment stages, a new three-dimensional model must be created that reflects the patient's dentition in the desired configuration. This involves capturing the shapes of individual teeth from the three dimensional plaster model into a computer aided design system. In the computer aided design system, the teeth are separated by a computerized process, and then reset in the desired configuration. The resulting computerized model of the patient's dentition in a desired configuration is then used to print a physical model of that tooth configuration. Finally, clear plastic which will form the aligner, such as a polyurethane, is molded over the physical model of the tooth configuration. Subsequent physical steps trim the molded aligner to remove sharp edges or portions which might contact and irritate the gingiva. In addition, the aligner surface and edges are typically smoothed via a process such as tumbling.

In some cases, attachments facilitate coupling of the aligners to the teeth. In the Invisalign® process, the attachments are placed using a template aligner that is thermoformed over a mold that matches the initial positions of the patient's teeth. Thin material can be used for the template aligner so that the template aligner is not as stiff or retentive as normal aligners. A "well" or "pocket" is created in the template aligner for each attachment. These "wells" are loaded with attachment composite and the template is fully seated on the patient's arch. Each attachment is then cured to the manufacturer's instructions. When all the attachments in the template have been cured, the template is removed and any flashing is removed with a carbide or stone finishing bur.

As can be seen, the fabrication of aligners is a tedious process which compounds both cost and time of treatment for the patient. Since such an orthodontic treatment may require, for example, 25 intermediate reset molds to represent 25 stages of treatment progress, the cost and time required for the necessary steps of mold making, aligner formation, and trimming, may be prohibitively high. The cost is additive, as each new stage in treatment or each change in treatment requires the production of a new mold. Likewise, the cost of storing a series of molds for each patient throughout treatment may be formidable.

U.S. Pat. No. 5,975,893, which is assigned to the proprietor of the Invisalign® product, and incorporated by reference herein in its entirety, describes the process elaborated above, and further, at end of the invention summary at col. 7 lines 15-29, the '893 patent states: "methods for fabricating a dental appliance according to the present invention comprise providing a first digital data set representing a modified tooth arrangement for a patient. A second digital data set is then produced from the first digital data set, where the second data set represents a negative model of the modified tooth arrangement. The fabrication machine is then controlled based on the second digital data set to produce the dental appliance. The fabrication machine will usually rely on selectively hardening a non-hardened resin to produce the appliance. The appliance typically comprises a polymeric shell having a cavity shape to receive and resiliently reposition teeth from an initial tooth arrangement to the modified tooth arrangement". The '893 patent provides no disclosure accompanying this statement, to indicate how to form the shape of such an appliance, or what material to use, and in commercial implementations, the owner of the '893 patent has always indirectly formed aligners from tooth models which are made by stereolithography as is described in the paragraphs preceding this one.

Treatment of malocclusion by aligners faces challenges other than the difficulty of manufacture. Specifically, aligners fastened with attachments may prove very difficult to install, as a result of the limited number of shapes that the attachment apertures on the aligner may take consistently with the Invisalign® manufacturing process; specifically, the attachment apertures must be formed by thermoforming over a stereolithographically-generated positive tooth model, which limits the type of apertures that may be made. Moreover, aligners may bind with the attachments and prove very difficult to remove.

Furthermore, in many aligner patients, the presence of the aligner within the patient's mouth causes a change in the points of occlusion between the mandible and maxilla, and in particular, causes the guidance of occlusion to move to the rear molars. This opens the patient's bite and typically intrudes the rear molars as a consequence of the unbalanced occlusion force on the rear molars. One result of this can be TMJ injury after the removal of the aligner because the force of the mandible is no longer resisted by the rear molars in the absence of the aligners.

For many patients aligners fabricated manually or by thermoforming on a positive model are uncomfortable and can irritate the patient's gingiva and/or tongue to such an extent that the soft tissue becomes inflamed and can potentially bleed. This discomfort is generally caused because the aligner is trimmed inaccurately to the patient's gingival margin. The inaccuracy in trimming is generally caused by the minimum size of the trimming tool particularly on the anterior lingual side where the aligner interferes with the tongue. Other anatomy such as the incisive papilla if not generally considered when trimming the aligner which can cause swelling or inflammation. In addition, the location where the aligner is trimmed can cause a sharp flange to be created at the base of the aligner near the gingival margin particularly on the lingual side.

It would be desirable to provide an alternative apparatus and methodology for realizing aligners configured to correspond to a series tooth configurations. Such apparatus and methods should be economical, reusable, reduce time consumption, reduce material waste, and, in particular, should reduce the need for fabricating multiple casts of teeth arrangements for stages in the orthodontic treatment. At least some of these objectives, as well as others, are met by the apparatus and methods of the invention described hereinafter.

SUMMARY OF THE INVENTION

The present application provides a detailed description of a method for direct fabrication of an orthodontic device having tooth-fitting cavities, such as aligner, using layer-by-layer printing of a polymeric material.

In specific embodiments disclosed herein, the tooth-fitting cavities are defined by the boundaries of the multiple layers, encapsulating up to fourteen teeth of a patient, and shaped to apply a load to at least one tooth that is sufficient to cause movement of the tooth, and remodeling of the adjacent bone. A series of such appliances may be used to treat malocclusion of teeth, each directly manufactured appliance used in series to incrementally move one or more teeth from initial positions toward a desired final position.

Alternately, the appliance may be a retainer that maintains tooth positions as defined by the cavities of the appliance.

The appliance may be formed of a single material, or may comprise layers of a first and a second polymeric material, each material forming part of the appliance. In another alternative, a second appliance, such as a stiffener, or an elastic member of wire or rubber, may be adhesively or otherwise joined to the directly manufactured appliance.

The direct manufacturing process permits appliances having a wider range of features and functions than has been possible with thermoformed appliances. For example, the directly manufactured appliances may be manufactured to include an aperture that a couples to an attachment on a patient's tooth, or may have an auxiliary shape integral to the appliance, such as a hook or button. Either may be used with a resilient element such as a rubber band to obtain an orthodontic function. The auxiliary shape may also be a cavity that fits over a second appliance mounted to a tooth, such as an orthodontic bracket, or a cutout from the appliance that fits over the tooth's crown.

The directly manufactured appliance may be manufactured so that the tooth cavities or other features have dimensionally controlled thickness, including a constant thickness or, as desired and mechanically/orthodontically useful, a variable thickness. Furthermore, the occlusal surfaces may be formed with variable thicknesses, such as a greater thickness on the distal area of the appliance and a lesser thickness on the proximal area of the appliance, for example, to create a guiding ramp for the teeth. This can, for example, unseal the tongue and soft palate of a sleep apnea suffer. Furthermore, occlusal surfaces may be made with a reinforced thickness, as compared to nonocclusal surfaces.

In one embodiment day and night appliances may be made in accordance with the principles of the present invention, to be worn alternately. The night appliance may have a greater thickness than the day appliance, e.g., the day appliance may have thickness a little as 0.15 millimeter and the night appliance may have thickness up to 1.0 millimeter. Alternately, or in addition, the day and night appliances may be of different materials.

An appliance made in accordance with principles of the present invention may be clear, or colored to a desired tooth appearance. Appliances may also be formed with a sequence identifier such as a number, letter or code, integrally formed in the appliance for reference by the patient or orthodontic practitioner.

Appliances made by the described method can be formed of polyurethane or a variety of other materials identified herein. In some embodiments, or with some materials, the appliance manufacture may involve a radiant energy curing step. Electron beam cross-linking may be used as well, and may be selectively applied to different extents at different portions of the appliance.

The computerized methods used in forming the appliance may include forming a mathematical model of the mandibular trough and aligning tooth shapes with the trough to form a tooth placement, and deriving the appliance from that tooth placement. The appliance may be formed by creating a surface that is offset from the tooth crown surface and solving for self-intersecting surfaces.

The manufacture of the appliance may be at a location geographically distant from the location where a digital model is created, including at the office of the orthodontic practitioner or the patient's home or place of work, permitting more rapid delivery of appliances to the patient and orthodontic practitioner.

The principles of the present invention further feature evaluating the stress of an appliance while mounted to a patient's teeth, by evaluating light refraction from the appliance.

The present application further discloses a method forming an appliance via thermoforming as is done in the prior art, using a mold created digitally, by forming a polymeric material in layers to create at least a portion of a mold having cavities for encapsulating teeth of the patient in desired final or intermedia positions, filling the polymeric material to form a positive cast of the repositioned teeth of the patient, then forming a plastic over the positive cast to create the appliance.

In specific embodiments of this aspect, at least some of the cavities of the mold and thus of the appliance may be shaped differently than corresponding teeth of the patient, e.g., the cavities may be relieved from the crown of one patient tooth. Further, the method may be adapted to form both day and night appliances having different thickness or made of different materials having different resilience characteristics. Furthermore, in specific embodiments the appliance may be colored to a desired tooth appearance and the steps of forming the appliance may be performed at a geographically remote location. Also, the use of appliances formed by each of the disclosed methods may be combined in a treatment plan to take advantage of the attributes of each type of appliance.

BRIEF DESCRIPTION OF THE DRAWINGS

The accompanying drawings, which are incorporated in and constitute a part of this specification, illustrate embodiments of the invention and together with the detailed description given below, serve to explain various aspects of the invention.

DETAILED DESCRIPTION OF THE INVENTION

Figure 3:
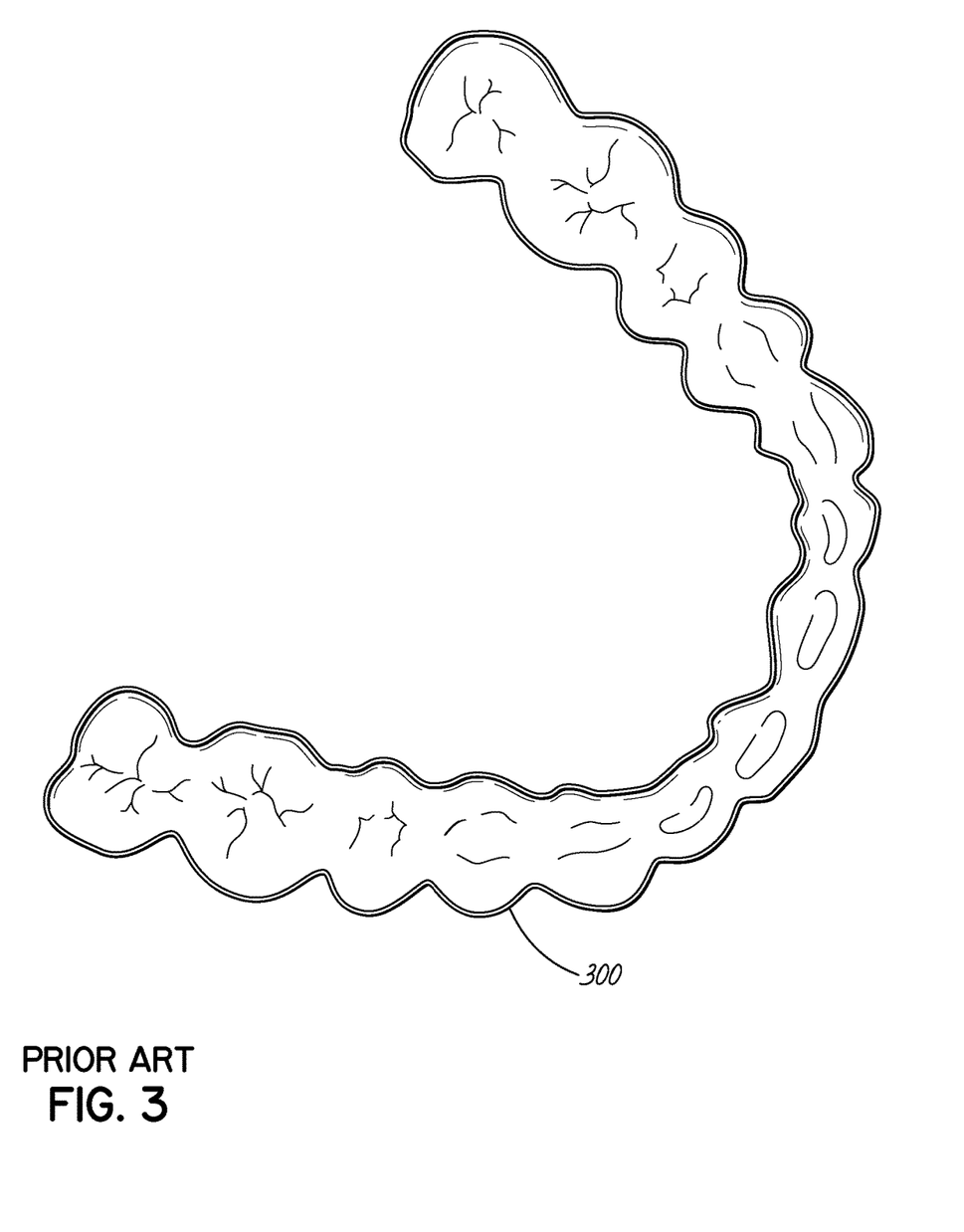
FIG. 3 is an illustration of an aligner formed using the 3D printer of FIG. 1 in accordance with the process of FIG. 2.
Figure 4:
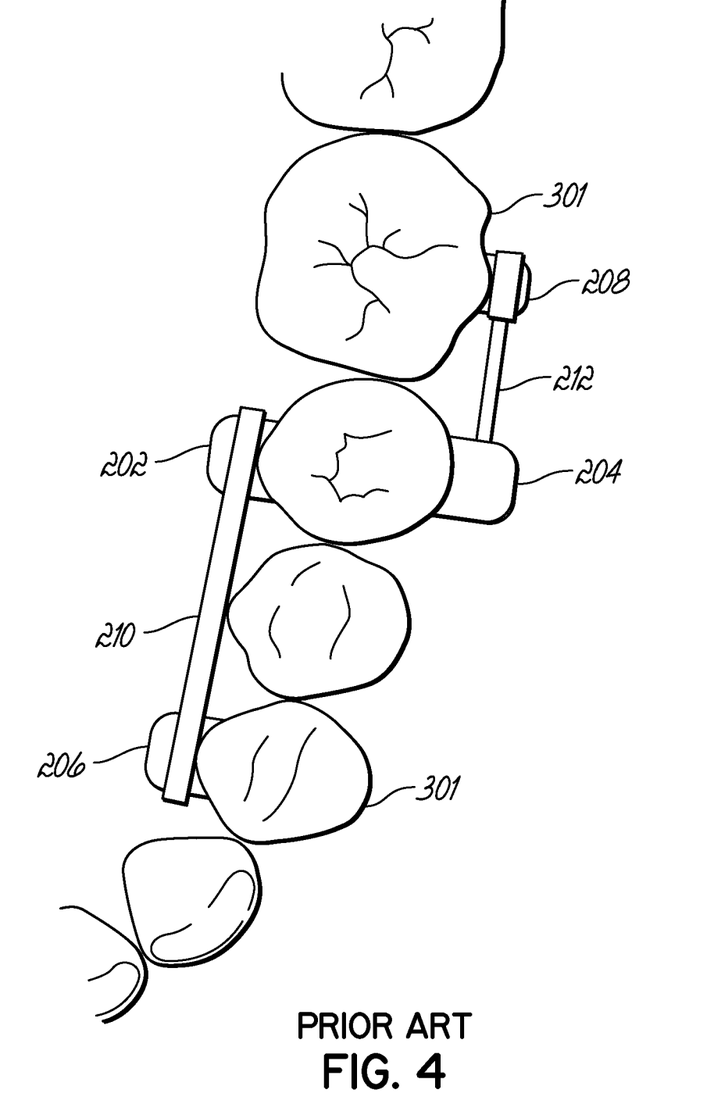
FIG. 4 is an illustration of an elastic used with buttons on an aligner formed using the 3D printer of FIG. 1 in accordance with the process of FIG. 2.

In general, one embodiment of the invention includes a directly manufactured orthodontic appliance capable of moving teeth according to a predetermined treatment plan, such as illustrated in FIGS. 3 and 4. In particular, the orthodontic appliance may move one or more teeth from one orientation to another which advances the overall orientation of the teeth toward their final orthodontically correct and aesthetically desired positions. In one embodiment of the invention, a series of individual orthodontic appliances may be utilized for complete orthodontic treatment. Accordingly, each appliance in the series may move one or more teeth a prescribed amount. Cumulatively, these individual amounts may result in complete treatment of the patient's malocclusion.

By way of example only, in one embodiment, the orthodontic appliance may include an aligner. Such aligners may be similar to those used in the prior art, but differ in the manner in which the aligner is made, and in detailed features, as is described below. The aligner may be configured to fit over or encapsulate multiple teeth on one of the mandible or maxilla.

In one embodiment, an aligner may be one of a series of aligners that are prescribed to treat a patient's malocclusion or a portion thereof by moving one or more teeth from the misaligned position toward their orthodontically correct position. For instance, the aligner, according to one embodiment of the invention, may move a single tooth or several teeth from one orientation to another orientation. This movement may be predetermined according to a treatment plan that includes a starting orientation and a final orientation. The starting orientation may be the initial orientation before treatment begins or any of the subsequent, intermediate tooth orientations as determined by a previous aligner or another orthodontic device. The final orientation for any aligner in a series of aligners may include a position that is intermediate between the starting orientation and the final orientation or it may be the functional and aesthetically pleasing position for the tooth observed at the conclusion of treatment.

In one embodiment of the invention, a system for treating a malocclusion may include a series of aligners differing in their configuration sufficient to fulfill a predetermined treatment plan. Each respective aligner may incrementally move one or more teeth from their misaligned positions toward or to their aesthetically correct or final orientation.

While embodiments of the invention include aligners that may not be secured to the patient's teeth with adhesives or such, it will be appreciated that the appliance, according to embodiments of the invention, may also be adhesively secured to the patient's teeth. Specifically, embodiments of the appliance may be adhesively joined to another orthodontic appliance and/or to the patient's teeth during orthodontic treatment. Furthermore, though not shown, it will also be appreciated that the appliance may alternatively be used on either or both of the maxilla and mandible.

By way of example, the aligner may substantially conform to one or more of the teeth on the jaw over which the aligner is placed. The aligner may encapsulate or nearly replicate the reverse shape of each tooth. However, there may be teeth in contact with the aligner that may not match or conform to the aligner on all surfaces of the tooth so that the aligner may provide a greater range of movement of those teeth in the direction where the aligner does not conform to the surface of the tooth.

Figure 1:
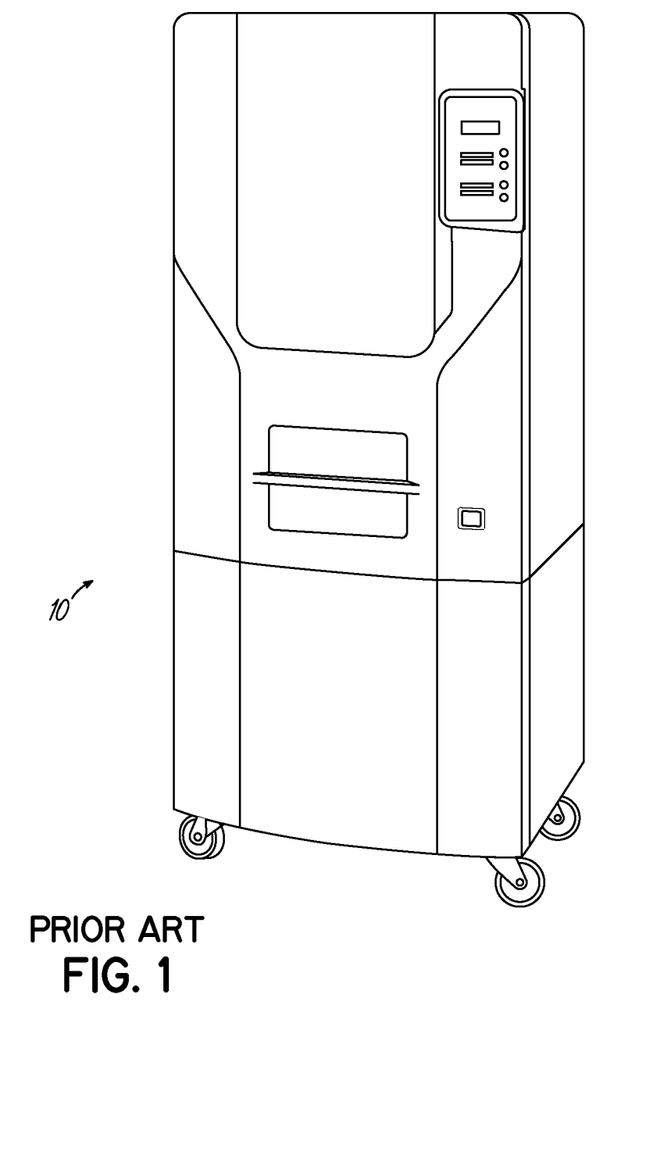
FIG. 1 is an illustration of a 3D printer suitable for implementing the present invention.

FIG. 1 illustrates a 3D printer 10 suitable for direct fabrication of an appliance in accordance with the principles of the present invention. The printer shown in FIG. 1 is a Dimension Elite 3D Printer, available from Dimension, Inc., a subsidiary of Stratasys, Inc., having an address of 7665 Commerce Way, Eden Prairie, Minn. 55344-2020 in the United States. This printer will print with P430 ABS polymer, using SR-30 soluble support material. The build size of the printer is in excess of 200 mm in three dimensions, which is easily sufficient for the printing of an aligner or other mouth-fitting appliance, indeed, it can be used to print several aligners or other appliances simultaneously (such the aligners for part of or an entire aligner sequence). The layer thickness printed by the printer is 0.178 mm or 0.254 mm, with a dimensional accuracy sufficient for orthodontic appliances. Although this printer may be useful for prototype purposes, for production Stratasys manufacture the Fortus 3D production systems for fast throughput and large build envelopes. In addition, these production systems make parts up to 300% stronger than the Dimension printer.

Figure 2:
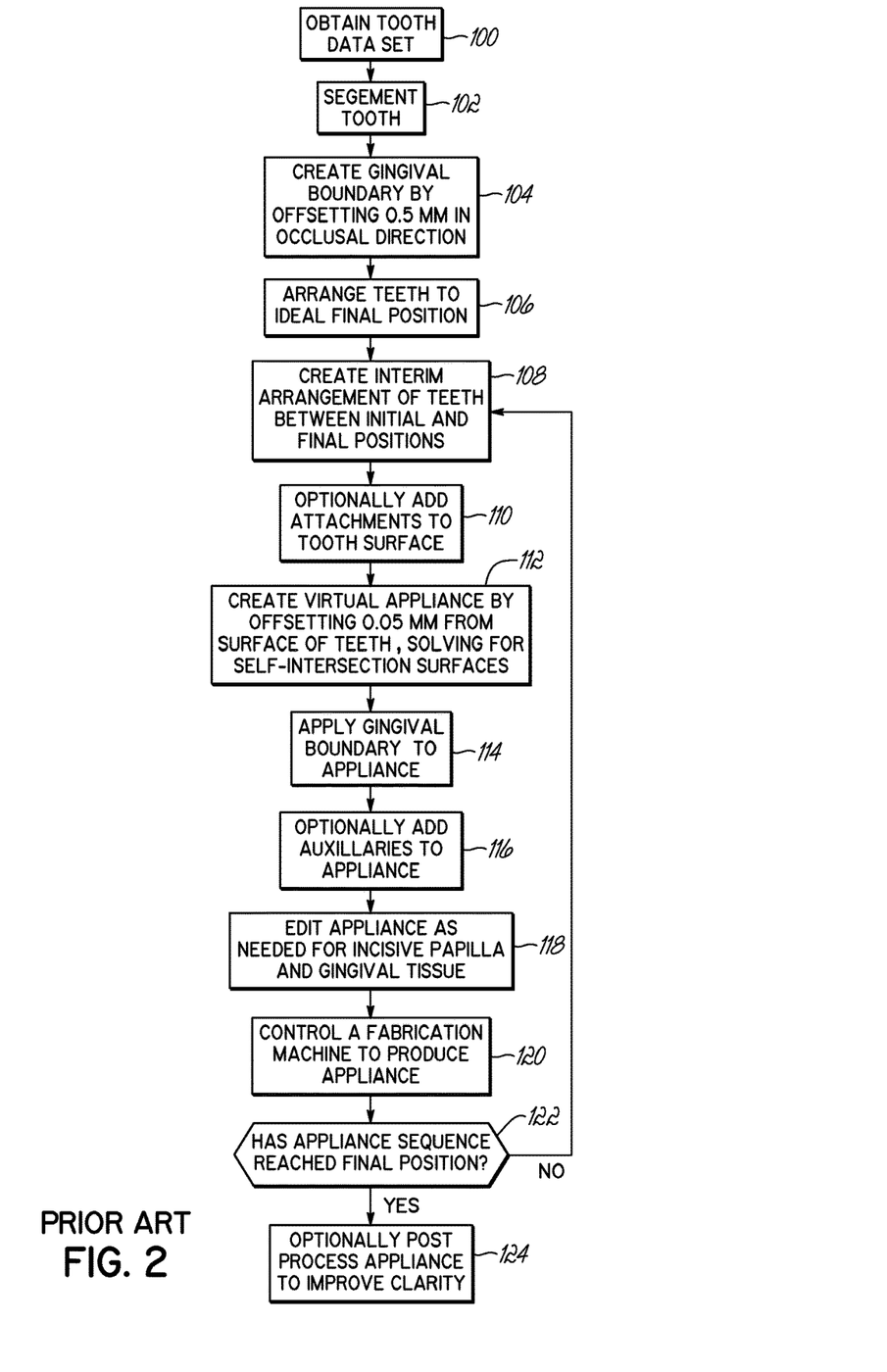
FIG. 2 is a flow chart of a manufacturing process in accordance with principles of the present invention.

FIG. 2 illustrates a flow chart of direct fabrication of incremental dental position adjustment appliances each representing incremental stages of an orthodontic treatment plan. The method comprises:

Step 100. Obtaining a data set representing the patient's initial tooth arrangement and gingival tissue. This step is performed generally by the methods disclosed in U.S. Pat. No. 6,616,444, which is incorporated by reference herein in its entirety, and assigned to the same assignee as this application.

Step 102. Segmenting the teeth to obtain individual data sets of each tooth located in their initial arrangement, in the manner disclosed by the incorporated U.S. Pat. No. 6,616, 444. In addition to the methods disclosed in the referenced Patent, where a tooth has a fixed sectional appliance applied, the body of the virtual tooth model may be extended to incorporate the band of the fixed sectional appliance such that the aligner may cover the fixed band when worn in the mouth. On teeth with fixed appliances in place, the boundary is determined by the type of fixed appliance. The aligner can be designed to cover the fixed appliance, a section of the aligner can be removed, or a combination of both for lingual and buccal sides. In the case of sectional bands, the boundary on the lingual side may follow the gingival but an aligner section may be removed on the buccal side similar to a button to allow for the fixed wire connecting the sectional bands.

Step 104. Creating a virtual boundary representing the patient's lingual and labial gingival margin offset by approximately 0.5 mm in the occlusal direction. This boundary represents the base of the appliance and can be edited using control points located at certain intervals. Control points can also be added and deleted as desired.

Step 106. Creating an arrangement of the individual teeth to represent an ideal final position using a mandible trough model calculation, and placement of teeth therein as disclosed in the incorporated U.S. Pat. No. 6,616,444. Alternatively, the final position can be generated by a manual process of moving teeth in a virtual model to align with a chosen, by automatically aligning teeth to a best fit to a chosen archwire, or in any other manual, partially automatic or fully automatic process.

Step 108. Creating interim arrangements of the teeth between the initial and final arrangements which incorporate tooth movements as can be generated by an aligner.

Step 110. Adding various three dimensional attachments to certain tooth geometry when the appliance is to be fitted over the same.

Step 112. Creating the virtual appliance's inner surface by offsetting "out" or shelling approximately 0.05 mm or more from the surface of each crown and solving for any self-intersecting surfaces. When neighboring crowns have sufficient space between them, the inner appliance surface will offset the mesial/distal surface of the crowns and the gingival surface between the crowns. When the distance is approximately 0.10 mm or less, the inner surface will terminate at the intersection of the surfaces near the occusal surface. Calculation of the outer appliance surface is provisionally 0.762 mm offset from the inner surface but can be increased or decreased overall or at targeted locations depending on the programmed movement of individual teeth.

Step 114. Applying the boundary previously calculated to the virtual appliance to form the base of the appliance.

Figure 4A:
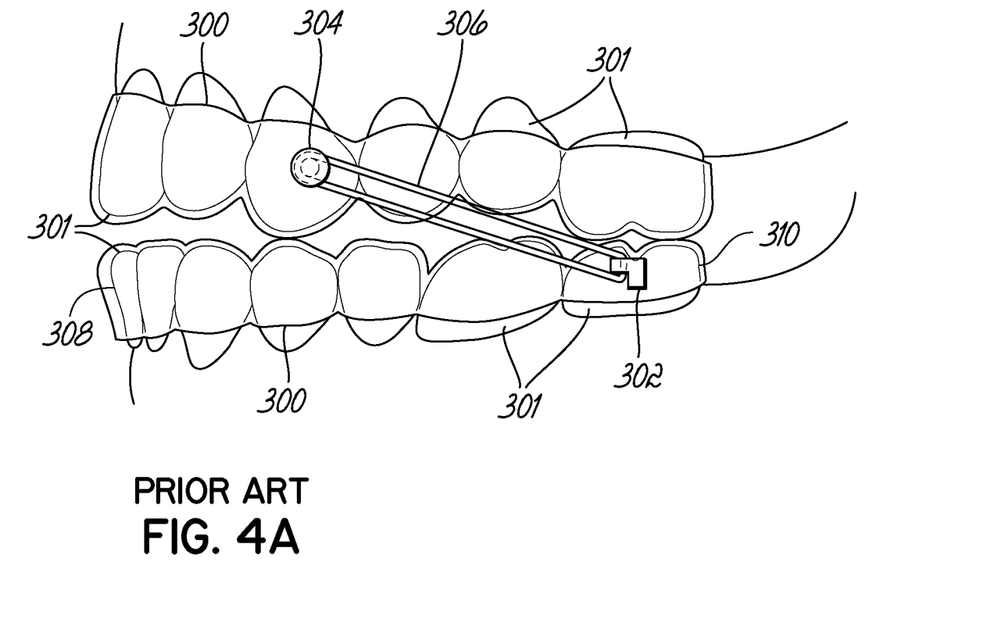
FIG. 4A is a side view of an aligner formed in accordance with the process of FIG. 2 and positioned on the teeth of a patient, showing the use of an auxiliary elastic mounting and elastic.
Figure 4B:
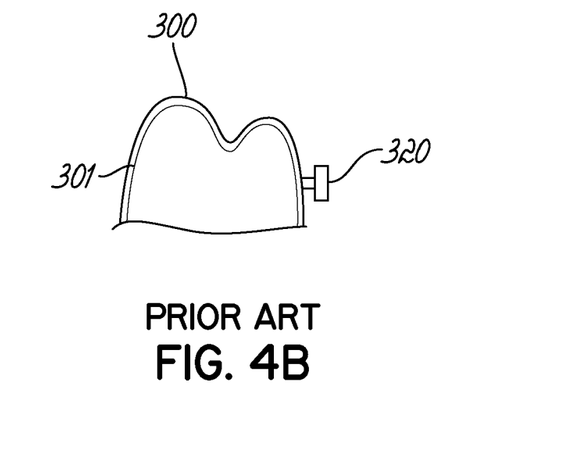
FIG. 4B is a cross sectional view of an aligner formed in accordance with the process of FIG. 2 showing auxiliary buttons for use with an auxiliary elastic.

Step 116. Modifying the virtual appliance shape if the appliance 300 will be used with auxiliaries such as buttons & elastics (see FIG. 4, buttons 202 and 206 and elastic 210, and FIGS. 4A and 4B, buttons 304 and 320 and elastic 306) and/or sectionals. Generally, if a button or bracket is cemented to a tooth and the appliance would cover that location, the appliance 300 will have a cutout to facilitate the button/bracket placement. The cutout can be achieved by modifying the boundary, generally with a semi-elliptical shape toward the occlusal, so the appliance is created to avoid the button. When using elastics attached to the button, the appliance will require an anchor so the elastic can be anchored to the appliance. The appliance anchor may take the form of a hook, which is cutout in the appliance shaped similar to a hockey stick approximately 2 mm long by 0.25 mm wide as is generally illustrated in FIG. 4A which shows an elastic 306 extending from a hook 302 in appliance 300, to a button 304 anchored to a tooth 301. The appliance anchor may alternatively take the form of a button 320 integrally formed in the surface of the appliance 300 as illustrated in FIG. 4B.

Auxiliaries and auxiliary mounts that may be manufactured integral to an aligner for purposes other than individual tooth movement, include A. Buttons or devices for capturing an elastic as seen in FIGS. 4, 4A and 4B as discussed above B. Tongue guidance devices for correction of sleep apnea disorders C. Other attachment points such as hook 302 shown in FIG. 4A to attach a functional device D. Class II correction ramps e.g. a Johnson twin block Step 118. Further manipulating the base of the appliance as required to avoid natural anatomy such as the incisive papilla and gingival tissue distal to the back molars.

Step 120. When editing is complete, using the virtual appliance object to control a fabrication machine to produce an appliance. By repetition of steps 108-120, a series of dental appliances is produced, leading from the initial to final position.

Step 122. Post-processing each appliance, as necessary depending upon the fabrication machine used to create the appliances, to improve the clarity of the appliance. 3D printing machines will generally require surface smoothing, which can be achieved by a number of mechanisms such as tumbling with silicon crystals or buffing with suitable polishes and then potentially coating with UV polymerized clear coat. Depending on the material, the appliances fabricated with SLA machines can be spun to remove the excess material and then baked in a radiant energy oven to cure the material. The process of curing the material may also remove any SLA build lines, consequently creating a clear aligner unmarred by build lines similar to Invisalign aligners.

The clear materials available for use with SLA and Polyjet printing machines generally do not have the same properties as thermoformed polyurethane. Clear polyurethane appliances are generally thermoformed with thickness of only 0.020-0.035 inches, and have sufficient tensile strength and elasticity to retain original shape necessary to move teeth and retain position over a period of time. To adjust for the material difference, a direct manufactured appliance in accordance with principles of the present invention, would be controlled in thickness to provide sufficient strength around the teeth that are programmed to move.

An alternative fabrication method may be employed to provide similar or potentially more advantageous aligner material properties than thermoformed polyurethane. Rather than direct manufacturing the aligner as previously described using SLA or 3D printing machines, the digital model of the aligner could be created as an injection mold similar to the practices used in rapid injection molding.

Yet another fabrication method would be creating a negative rather than a positive mold of the tooth arrangements and the negative mold could be employed in thermoforming the aligner.

Figure 6:
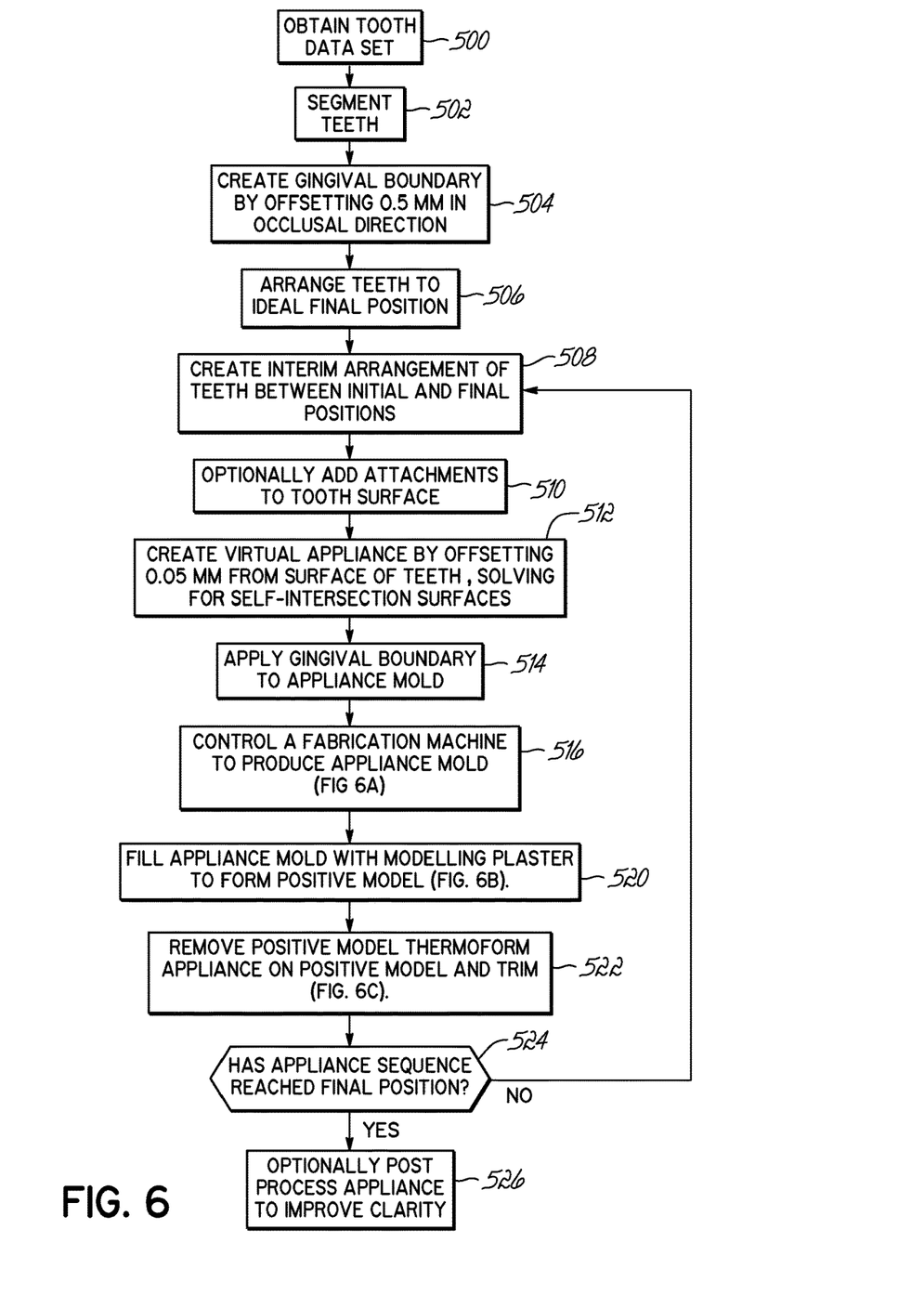
FIG. 6 is a flow chart of a manufacturing process in accordance with a second aspect of the present invention.

Still a further alternative embodiment of the invention is a thermoforming process that is further indirect, which uses direct manufacturing to create a mold from which a positive model can be created, from which the appliance may be thermoformed. Referring to FIG. 6, in this process, the aligner mold is formed from a stereolithgraphic process, cured, and then affixed to a base and used to form a positive model, as set for the in the steps of FIG. 6:

Step 500. Obtaining a data set representing the patient's initial tooth arrangement and gingival tissue, by the methods disclosed in the incorporate U.S. Pat. No. 6,616,444.

Step 502. Segmenting the teeth to obtain individual data sets of each tooth located in their initial arrangement, in the manner disclosed by the incorporated U.S. Pat. No. 6,616,444. In this step, as in step 102, the body of the virtual tooth model may be extended to cover the fixed appliances on the patient's teeth when worn in the mouth, or a section of the aligner can be removed, or a combination of both for lingual and buccal sides.

Step 504. Creating a virtual boundary of the appliance mold, representing the patient's lingual and labial gingival margin offset by approximately 0.5 mm in the occlusal direction, as in step 104 discussed above.

Step 506. Creating an arrangement of the individual teeth to represent an ideal final position using a mandible trough model calculation, and placement of teeth therein as disclosed in the incorporated U.S. Pat. No. 6,616,444, or a manual process, as in step 106.

Step 508. Creating interim arrangements of the teeth between the initial and final arrangements which incorporate tooth movements as can be generated by an aligner, as in step 108.

Step 510. Adding various three dimensional attachments to certain tooth geometry when the appliance is to be fitted over the same, as in step 110.

Step 512. Creating the virtual appliance mold's inner surface by offsetting "out" or shelling approximately 0.05 mm or more from the surface of each crown and solving for any self-intersecting surfaces, as in step 112. This inner surface offset may be different for this process than when directly fabricating an aligner, for example, to compensate for expansion of the poured modeling material used in the steps that follow.

Step 514. Applying the boundary previously calculated to the virtual appliance to form the base of the appliance mold.

Figure 6A:
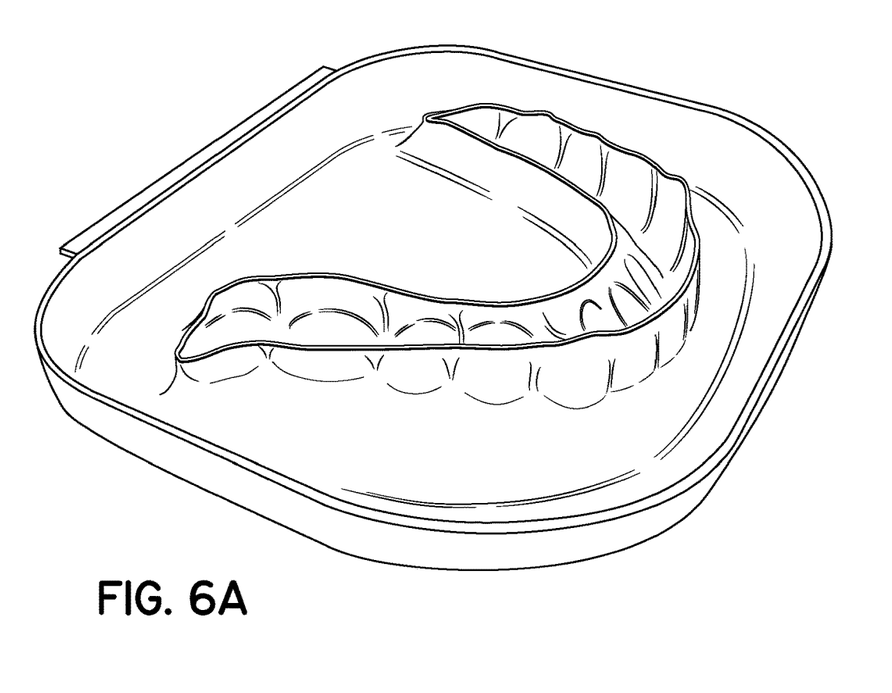
FIG. 6A is an illustration of a first manufacturing step in the process illustrated in FIG. 6.

Step 516. When editing is complete, using the virtual appliance mold object to control a fabrication machine to produce an appliance mold. The appliance mold may be built integrated with a support tray, as seen in FIG. 6A, to facilitate handling and the filling of the mold in the following steps.

Figure 6B:
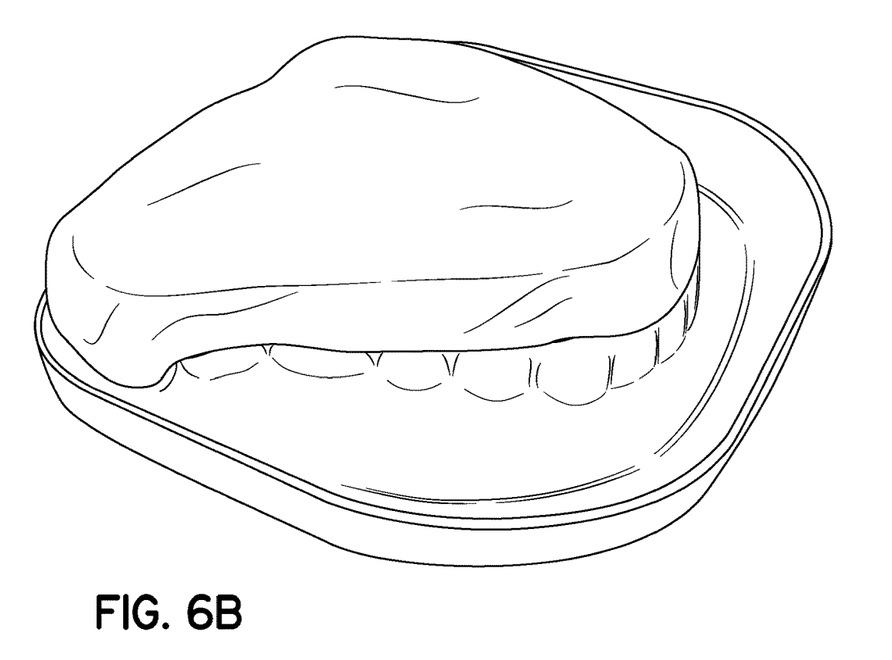
FIG. 6B is an illustration of a second manufacturing step in the process illustrated in FIG. 6.

Step 520. Filling the appliance mold as seen in FIG. 6B with modeling plaster, dental stone, plastic, resin or another suitable material to form a positive model of the patient's teeth and gingival.

Figure 6C:
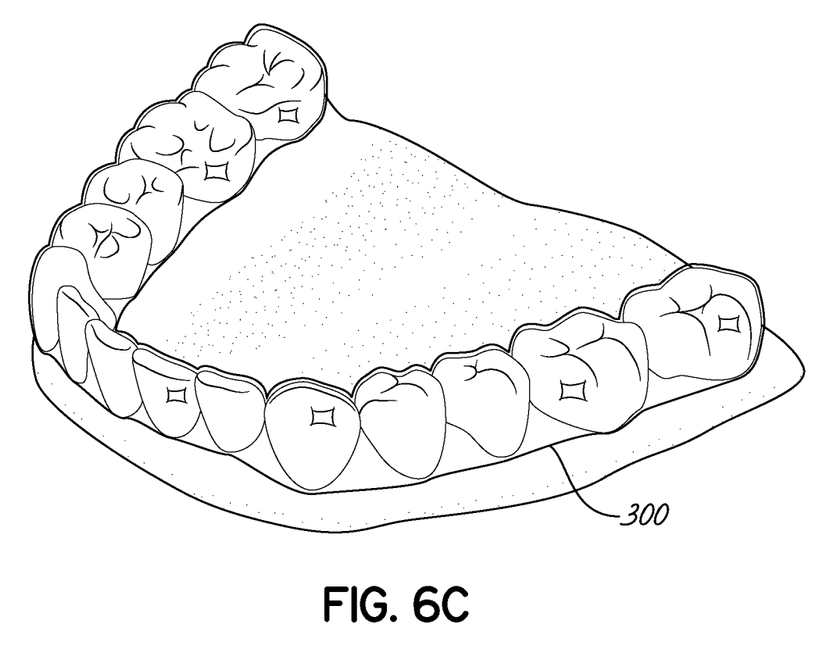
FIG. 6C is an illustration of a third manufacturing step in the process illustrated in FIG. 6.

Step 522. Removing the positive model from the mold, and then thermoforming any suitable clear plastic upon the positive model (as seen in FIG. 6C) and trimming the same to arrive at the appliance.

Step 524. Repeating for an additional appliance for an incrementally advanced tooth position.

Step 526. Post processing of the appliances, such as tumbling as discussed above.

By repetition of steps 508-524, a series of dental appliances may be produced, leading from the initial to final position.

This alternative method has the advantage that the material used in the stereolithgraphic/rapid prototyping machine to form the appliance mold can be any suitable material without requirement of specific material properties. It may be advantageous to use brittle materials with minimal thickness to facilitate the extraction of the positive model from the mold by breaking the brittle mold.

As the material thickness increases, the appliance may become more noticeable in the mouth so not achieve one of its primary goals of being clear and unnoticeable when worn. In such cases a series of thicker appliances can be manufactured which will be worn at night to achieve the programmed movements and a series of clear 0.02-0.035 inch appliances will manufactured and worn during the day to retain the movements delivered during the night. By this combination of day and night appliances, the programmed movements may achieve even greater efficacy than can generally be achieved by appliances currently marketed.

The direct manufacturing process described above allows direct control over appliance thicknesses in certain locations so movements that might have previously been unpredictable can benefit from using thicker material at targeted locations on the aligner.

Additionally, since the process of forming an appliance is digital, the described method enables distributed manufacturing, in strategically selected locations throughout the world, based on appliance models formed in a central location.

Appliances created by the direct manufacturing process may incorporate decorative or identification features, such as patient identification numbers, logos, and coloring in the fabricated aligner material providing an appearance of whiter, corrected teeth. In addition, the front surface of the aligner may be formed with the appearance of aesthetically pleasing straightened teeth, while the cavities therein encapsulate the patient's actual teeth for corrective purposes.

Appliances made by the above-noted processes may be variably cross linked. Specifically, the cross-linking of the material could be tuned to produce the visco-elastic behavior for optimal tooth movement. The cross-linking could be controlled in the material that forms an aligner, to obtain an ideal visco-elastic behavior. Urethanes, in particular, can be selectively cross-linked with an electron beam. This could be used to cross-link different parts of the aligner to different levels. For example, particular tooth cavities, or the vicinity of an attachment hook, may be differently cross-linked as compared to other tooth cavities or areas.

It will be appreciated that teeth are visco-elastically bound. Aligners displace teeth near to the possible extreme of the Periodontal Ligament. This displacement eventually causes the cellular response that converts the bone in the mandible or maxilla into tissue permitting tooth movement. The aligner material visco-elasticity interacts with the visco elasticity of the teeth, an interaction which has an optimum balance in which the tooth is at a moved position. There is a latency before this effect takes hold, after which, the movement then can continue fairly regularly because the cellular process has begun. Note that in adults it can take much longer than 2 weeks for the process to get started, in children it takes less time. The aligner stiffness and geometry, and the replacement timing, can be adjusted for interaction with the physiology of tooth movement.

In an aligner in accordance with the present invention, the tooth cavities would not necessarily mate to the surface of the tooth—rather, the surface may be relieved away from the crown in the direction that movement is being sought, and be closer on the opposite side. This may have beneficial effects compared to a cavity that has a shape conforming to the crown of the tooth, because it may be able to apply greater force in the direction of desired tooth movement, over a longer time period, without counterbalancing force from the aligner cavity wall on the opposite side of the tooth.

In an aligner that is directly manufactured in accordance with FIG. 2 of the present invention, another advantage is that the aligner should not require trimming, thus avoiding steps. Specifically, no step need be taken to avoid edges that might injure gingiva, as those edges are electronically removed prior to formation of the aligner. Further, a tumble process on the aligners may not be needed, or needed as much, as a main purpose of tumbling is to remove sharp edges that form from trimming. In an aligner directly manufactured in accordance with the present invention, these edges are not formed in the first instance.

In an aligner in accordance with the present invention, it is possible to programmatically control the clearance of the aligner relative to the teeth. This should reduce the number of failed cases and/or make manufacturing more streamlined.

In an aligner in accordance with the present invention, because the aligner can be directly fabricated with a shape that directly matches the attachment, the use of attachments may be improved. E.g., the direct manufactured aligner can match the attachment closer than in conventional aligners. Moreover, attachments might be smaller as a result, and cause them to interlock better, and the features and shapes could be more optimized for the attachments.

An aligner in accordance with the present invention may include a socket that is perfectly fitted to an attachment for adding or altering forces. Or an aligner can be made in separate parts to be mechanically joined such as by block 204 seen in FIG. 4, to mechanical intermediaries such as the shaft 212 seen in FIG. 4 which mounts at 208 to a bracket on another tooth 301 or on an appliance mounted to the tooth 301. The aligner may include many manufactured features such as handles, tabs, lugs, and cams, not limited to the particular features shown here.

An aligner directly manufactured in accordance with the present invention may include a number of features to aid in the capture of an attachment and also aid in removal off an attachment. A living hinge spring for capturing the attachment could improve the force applied and also make it easier to release from the attachment.

The direct manufacture of the attachment-interacting structures on the aligner allows control of the amount of force that would be required for the removal of the aligner, as compared to the conventional process which often requires too much force to remove an aligner.

A problem with aligners is that in many aligner patients, the aligner intrudes the rear molars because the presence of the aligner opens the patient's bite. The result is often TMJ injury because the force of the mandible is not being resisted by the rear molars after the removal of the aligner. This can be corrected in a directly manufactured appliance, which could be made thicker at the mesial occlusal surface than at the distal occlusal surface. Referring to FIG. 4A, it can be seen that an appliance 300 has a thicker profile at the distal occlusal surface 308, than at the mesial occlusal surface 310, thus providing compensation for the presence of the aligner to alleviate impacting of the molars in the mesial area 310 resulting from the use of the appliance.

In certain circumstances, the occusal surface of the aligner could be removed entirely for some targeted teeth for the entire treatment or for certain interim stages during the treatment. In such cases, it may be necessary to increase the thickness of the aligner on the body of such teeth to ensure structural integrity of the aligner.

Taking this principle further, the aligner can also form a functional appliance, giving class 2 correction on the bite, moving the mandible forward or rearward because the occlusal appliance surfaces are ramped relative to each other.

The aligner could also perform the functions of a sleep apnea appliance. This version of the appliances would include ramps on the maxillary or mandibular appliance, which interact, driving the mandible forward when worn. (Studies have shown that 2-3 millimeters of mandible motion is enough to prevent a seal between the tongue and soft palette which can cause the onset of sleep apnea.)

An aligner in accordance with the present invention might include a tongue crib on the interior of the upper tray to retrain the tongue to not push on front teeth. (Patients with front tooth gaps often have the need to retrain their tongue.)

Aligners often crack on the occlusal surfaces. An aligner in accordance with the present invention could include custom loading surfaces on the contact points to prevent such cracking. Patients who grind their teeth, in particular, can also be prescribed for this aligner enhancement.

Figure 5:
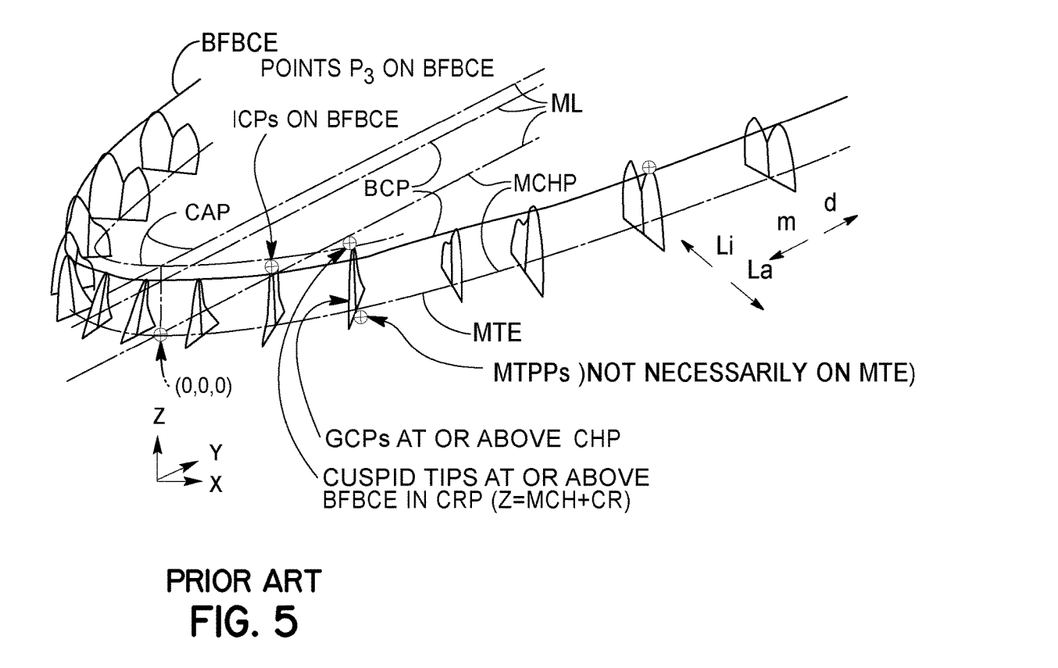
FIG. 5 illustrates a calculation of an equation to describe the medullary center of a patient's mandibular bone and placement of crown long axes of mandibular teeth at specified inclinations and roots centered in the mandibular trough, as part of the computation of desirable tooth positions as further elaborated in U.S. Pat. No. 6,616,444, which is incorporated herein by reference in its entirety.

Also, in an aligner in accordance with the present invention, mandibular trough modeling may be implemented as part of building of the aligner. An equation for the mandibuloar trough is mathematically calculated, representing the medullary center of the mandibular bone, using the calculations elaborated in the incorporated U.S. Pat. No. 6,616,444 and illustrated in FIG. 5. The mandibular teeth are placed on the curve such that the crown long axes are at specified inclinations, as opposed to the facial inclinations that have been used to date. The centric stops (buccal cusps) of these teeth are aligned on another smooth equation derived from mandibular trough, such that the roots of the teeth are centered in the bone. The maxillary teeth are then placed in occlusion with the already-set mandibular teeth.

Maxillary posterior teeth are placed with respect to centric stops and calculations for molar rotation, as explained in the incorporated U.S. Pat. No. 6,616,444. The maxillary anterior teeth are placed from calculations to provide either group function or cuspid rise parameters. Other calculations regarding tooth-size discrepancies, depth of bite, etc., are also done at this time.

Sectional or partial aligners may also be formed in accordance with the present invention. In conventional processes, an aligner is thermoformed in one piece and segmented to create fixed sectional appliances or Biobloc appliances. Unfortunately, however, this process can compromise the structural integrity of the aligner, causing the aligner to crack or break when inserted or removed from the mouth. In addition, retention of the aligner is likely to be compromised in the quadrant cut to facilitate the sectional appliances which may substantially reduce the efficacy of the desired movements in a different quadrant. Using direct manufacture, the sectional appliances may be separately formed, avoiding compromise in structural integrity.

In accordance with this aspect, the manufacturing process may utilize data regarding sectional appliances already in place in manufacturing the aligners to be used in combination with the sectional appliances. The formation of the aligner boundary takes account of present sectional appliances. Specifically, on teeth with fixed appliances in place, the boundary is influenced by the type of fixed appliance. The aligner can be designed to cover the fixed appliance, a section of the aligner can be removed, or a combination of both for lingual and buccal sides. In the case of buttons for elastics or fixed wires, a section of the aligner is generally removed so the boundary would not follow the gingival for that tooth but would be moved toward the occlusal in an arch shape around the fixed button. In the case of sectional bands, the boundary on the lingual side may follow the gingival but an aligner section may be removed on the buccal side similar to a button to allow for the fixed wire connecting the sectional bands.

The recent development of temporary anchorage device (TAD) concepts in orthodontics is also applicable to aligners. The use of cutouts for buttons and elastics detailed in step 116 and illustrated in FIG. 4A, can also be used with TADS to help anteroposterior discrepancies and also create favorable anchorage beyond the capabilities of the aligner alone to facilitate additional tooth movement such as impacted canines, incisor torquing, distalization or molar uprighting. Sectional or Biobloc appliances may allow most malocclusions to be treated with aligners: deep bites, severe rotations, bodily movement, and distalization/mesialization of posteriors are difficult to correct with aligners alone or even aligners with the use of elastic auxiliaries. The ability to use aligners simultaneously with sectional appliances speeds up treatment significantly and allows most malocclusions to be treated with clear aligners where today clear aligners can only be used in mild to moderate cases for most practitioners.

Finally, the manufacturing process according to the present invention may also permit stress analysis. A rainbow effect appears in polyurethane plastics when heated, Illuminated with polarized white light and viewed with polarized filter. Changes in refractive index as a result of strains in the plastic create the rainbow effect. The rainbow thus correlates with the locations of strain in the plastic, and these strains can be seen with a polarized lens. Birefringence could be a way to see the strain pattern via the rainbow effect in an aligner when placed in the patient's mouth. Taking advantage of this effect, patients could, using polarized glasses, view light from aligner to evaluate stress, and return to the orthodontist/dentist whenever there is a certain pattern in the aligner (e.g., loss of stress at a key tooth indicating movement has completed).

A variety of polymers and printing technologies may be used in accordance with principles of the present invention.

3D Systems, of Rock Hill, S.C. offers several resin formulations for example: Accura 60, Accura ClearVue, and RenShape 7870 which are transparent, and are quite tough. Clearvue is designated as bio-compatible. 7870 has published impact strength of 0.85-1.15 ft-lbf/in. Accura 60 has a tensile strength similar to thermoformed polycarbonates of 58-68 MPa and flexural strength of 87-101 MPa. Accura ClearVue has a tensile strength of 41-44 MPa and flexural strength of 74-79 MPa. SL 7811 has an elongation at break value of up to 30% although it is white, not transparent, but it may be possible to reformulate it to create a transparent and bio-compatible material. In addition, there is potential to reformulate certain materials to enhance the desirable properties of aligner materials.

Objet, of 5 Fortune Drive, Billerica Mass. 01821 offers several materials which are transparent and also designated as bio-compatible; FullCure 630 and FullCure 810 which could be used to form aligners using 3D printing machines from Objet.

DSM Somos of 2 Penns Way, Suite 401, New Castle, Del. 19720 has formulated resins for the stereolithography market for many years. It offers three transparent materials, certified biocompatible for cytotoxicity, sensitization, and irritation: WaterShed 11122, ProtoGen 18420, and BioClear. All three have published impact strengths of 0.4-0.6 ft-lbf/in. WaterShed XC 11122 is waterproof.

DWS, of Zané, Vicenza Italy, manufactures vat photopolymerization systems. Its process creates parts by exposing a light-curing photopolymer to an ultraviolet light source. The parts are built under a build platform by solidifying photosensitive resin through a special transparent tank using a solid-state laser. DWS has developed a transparent material for surgical guides that will be certified to the cytotoxicity, sensitization, and irritation biocompatibility tests.

Asiga of 155 North Riverview Drive, Suite 100, Anaheim Hills, Calif. 92808 makes a system called the Pico FreeForm. Its PlasClear material is transparent. The company is in the process of scheduling ISO 10993 testing of external (hearing aid) applications and testing for internal medical devices is planned.

EnvisionTEC GmbH of Bursseler Str. 51, D-45968 Gladbeck, Germany offers e-Shell 300, a transparent bio-compatible material approved for hearing-aid applications.

Dreve Dentamid GmbH of Max-Planck-Str. 31, 59423 Unna, Germany formulates its own materials and offers additive manufacturing systems from a subsidiary named Innovation MediTech. The systems, called FotoMed LED, use LEDs and digital light processing (DLP) to cure photopolymer. Its FotoMed LED material is transparent, strong, and hard. It meets the ISO 10993 criteria for cytotoxicity, sensitization, and irritation testing.

Stratasys Inc., at the address identified above, offers materials that are bio-compatible; ABS-M30i and PC-ISO, but neither is transparent. The ABS-M30i thermoplastic has impact strength of 2.6 to 5.3 ft-lbf/in, which is higher than most other candidate materials. Although Stratasys does not currently offer transparent materials, of all the additive manufacturing systems, Fusion Deposition Modeling (FDM) might have the most potential for use with materials whose properties are similar to the thermoplastics used to thermoform aligners. For example, materials used to thermoform aligners such as Zendura, Duraclear, Tri-Plast and Biocryl could be modified for use with an FDM machine to fabricate aligners with very similar mechanical properties to thermoformed aligners. In addition, post-processing techniques such as ultrasonic bath and tumbling with ceramic cones might yield similar transparent qualities as the thermoformed aligners. In addition, since the material was initially bio-compatible, the result of reformulating these thermoplastic materials for use in FDM machines would likely result in similar characteristics.

While the present invention has been illustrated by a description of various embodiments and while these embodiments have been described in some detail, it is not the intention of the inventor to restrict or in any way limit the scope of the appended claims to such detail. Thus, additional advantages and modifications will readily appear to those of ordinary skill in the art. The various features of the invention may be used alone or in any combination depending on the needs and preferences of the user.

What is claimed is:

1. A method of orthodontically treating a patient's teeth, comprising
developing a digital model of the patient's teeth in their present positions;
forming a polymeric material in a series of layers to collectively form at least a portion of an appliance mold, the appliance mold comprising plural cavities for encapsulating teeth of the patient when repositioned from their present positions;
filling the polymeric material to form a positive cast of the repositioned teeth of the patient;
forming a plastic over the positive cast to create the appliance; and
placing the appliance on the patient's teeth.

2. The method of claim 1 wherein the appliance mold cavities are each formed from a boundary of several of said series of layers.

3. The method of claim 1 wherein at least one mold cavity is shaped similar to a shape of first tooth of the patient, and a second mold cavity is positioned in the appliance to fit to a second tooth of the patient but does not have a similar shape as the second tooth.

4. The method of claim 3 wherein the second cavity has a shape that is relieved from the crown of the second tooth on one side thereof.

5. The method of claim 1 wherein forming the polymeric material further comprises radiant energy curing of the polymeric material.

6. The method of claim 1 wherein the appliance has a first thickness, and further comprising fabricating a second appliance having a greater thickness than the first thickness.

7. The method of claim 6 wherein the first thickness is no less than approximately 0.15 millimeters and the greater thickness of the second appliance is no greater than approximately 2.0 millimeter.

8. The method of claim 1 wherein the appliance is formed of a first material, and further comprising forming a second appliance, the second appliance utilizing a second material.

9. The method of claim 1 wherein the appliance is colored.

10. The method of claim 1 wherein forming the appliance further comprises electron beam cross-linking of the material that forms the appliance.

11. The method of claim 10 wherein the electron beam cross-linking is selectively applied to different extents at different portions of the appliance.

12. The method of claim 1 wherein forming the appliance further comprises forming a mathematical model of the mandibular trough and aligning tooth shapes with the mandibular trough to form a tooth placement, and using the tooth placement to form the appliance.

13. The method of claim 1 wherein the step of forming the appliance is performed at a location that is geographically distant from the location where the step of developing a digital model is performed.

* * * * *